US006849461B2

(12) United States Patent
Eigen et al.

(10) Patent No.: US 6,849,461 B2
(45) Date of Patent: *Feb. 1, 2005

(54) METHOD AND DEVICE FOR THE SELECTIVE WITHDRAWAL OF COMPONENTS FROM COMPLEX MIXTURES

(75) Inventors: Manfred Eigen, Göttingen (DE); Rudolf Rigler, Dandöryd (SE); Karsten Henco, Erkrath (DE)

(73) Assignee: Evotec OAI AG, Hamburg (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/750,715

(22) PCT Filed: Jun. 16, 1995

(86) PCT No.: PCT/EP95/02344
§ 371 (c)(1),
(2), (4) Date: Mar. 19, 1997

(87) PCT Pub. No.: WO95/35492
PCT Pub. Date: Dec. 28, 1995

(65) Prior Publication Data
US 2002/0073787 A1 Jun. 20, 2002

(30) Foreign Application Priority Data
Jun. 17, 1994 (DE) ........................ P 44 22 313
Jun. 25, 1994 (DE) ........................ P 44 22 290

(51) Int. Cl.[7] ........................ G01N 21/84; G01N 33/15; G01N 1/14; G01N 21/64; G01N 21/75
(52) U.S. Cl. ................ 436/180; 73/863.01; 73/866; 356/36; 356/300; 356/344
(58) Field of Search .................... 73/864.16–864.21, 73/863, 863.01, 864.81, 866; 356/36, 300, 344; 436/63, 174, 180

(56) References Cited

U.S. PATENT DOCUMENTS

| 4,756,427 A | | 7/1988 | Gohde et al. ................ 209/3.1 |
| 4,784,147 A | * | 11/1988 | Mosfeghi ..................... 600/425 |
| 4,784,737 A | | 11/1988 | Ray et al. ................ 204/180.1 |

(List continued on next page.)

FOREIGN PATENT DOCUMENTS

| DE | 370711 A1 | | 9/1988 | |
| EP | PCT/EP94/00117 | | 1/1979 | ............ B05B/7/32 |
| WO | WO 94/10564 | * | 5/1994 | .......... G01N/30/30 |
| WO | WO 94/16313 | * | 7/1994 | .......... G01N/21/64 |

OTHER PUBLICATIONS

*Patent Abstracts of Europe* "Method and Device for Assessing, the Suitability of Bio Polymers" (WO–09416313A2) Jul. 21, 1994 by Rudolf Rigler et al.*

(List continued on next page.)

*Primary Examiner*—Thomas P. Noland
(74) *Attorney, Agent, or Firm*—Jacobson Holman PLLC

(57) ABSTRACT

The method according to the invention permits a selected withdrawal of one or a few molecularly disperse or cellular components of a system, such as molecules, molecular complexes, vesicles, micelles, cells, optionally together with an associated volume element V having a size of $10^{-9} 1 \geq V \geq 10^{-18} 1$ from a larger sample volume. The selected transfer of the sought component to another environment is effected by defining the space and time of withdrawal by means of a signal correlating with the small component to be withdrawn. The method is particularly useful for the withdrawal of non-abundant components the existence of which can be detected in a preceding step by a scanning process. The method is also useful for the withdrawal of per se unidentified components.

21 Claims, 5 Drawing Sheets

Figure 1:
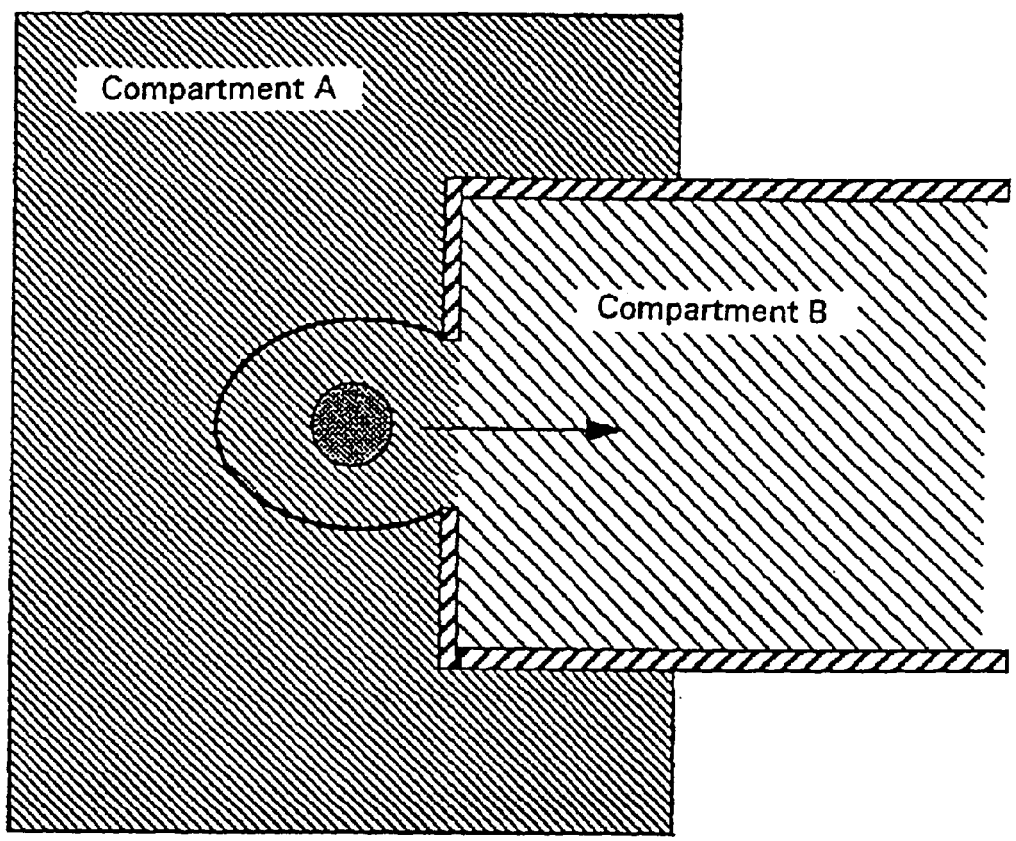

FCS Selection of Individual Microorganisms with Selected Fractioning (FCS Molecule Sorting)

U.S. PATENT DOCUMENTS

| | | | | |
|---|---|---|---|---|
| 4,887,721 | A | | 12/1989 | Martin et al. ............... 209/579 |
| 5,030,002 | A | | 7/1991 | North, Jr. .................... 356/73 |
| 5,239,178 | A | * | 8/1993 | Derndinger et al. ........ 250/234 |
| 5,250,188 | A | * | 10/1993 | Bruening et al. ........... 210/672 |
| 5,288,999 | A | | 2/1994 | Betzig et al. .......... 250/227.26 |
| 5,571,398 | A | * | 11/1996 | Karger et al. ............... 204/603 |
| 5,587,832 | A | * | 12/1996 | Krause ....................... 359/385 |
| 6,582,903 | B1 | * | 6/2003 | Rigler et al. ............. 356/36 X |
| 2004/0142386 | A1 | * | 7/2004 | Rigler et al. ................. 435/7.2 |

OTHER PUBLICATIONS

Gerd Weber et al, "Manipulation of Cells, Organelles, and Genomes by Laser Microbeam and Optical Trap", International Review of Cytology, vol. 133, pp. 1–41, dated 1992 no month given.

A. Ashkin et al., "Optical trapping and manipulation of single cells using infrared laser beams", Nature vol. 330 24/31, Dec. 1987, pp. 769–771.

Manfred Eigen et al., Sorting single molecules: Application to diagnostics and evolutionary biotechnology, Proc. Natl. Acad. Sci. USA, vol. 91; pp. 5740–5747, Jun. 1994.

Anderson, "Confocal laser microscopes see a wider filed of application," *Laser Focus World*, 30(2):83–86 (Feb. 1994).

Oian et al., "Analysis of confocal laser–microscope optics for 3–D fluorescence correlation spectroscopy," *Applied Optics*, 30(10):1185–1195 (Apr. 1991).

Tiziani et al., "Three–dimensional image sensing by chromatic confocal microscopy," *Applied Optics*, 33(10):1838–1843 (Apr. 1994).

Rigler et al., "Interactions as Observed by Fluorescence Correlation Spectroscopy," *Fluorescence Spectroscopy, New Methods and Applications*, 92/23815 (Dec. 6, 1992).

Rigler et al., "Diffusion of Single Molecules Through a Gaussian Laser Bean," *Laser Spectroscopy of Biomolecules*, 1921:239–247 (Sep. 1992).

Rigler, Rudolph and Metr, Ulo, *"Diffusion of Single Molecules Through A Gaussian Laser Beam"*, *SPIF– The International Society for Optical Engineering*, vol. 1921, (1993), 239–47, month not given.

Nagourney et al., *"Shelved Optical Electron Amplifier: Observation of Quantum Jumps"*, *The American Physical Society*, vol. 56, (1986), 2797–99, No. 26, Physical Review Letter, June.

* cited by examiner

Virus X in acute
viremic phase

Virus X in
chronic phase
(patient 1)

anti X IgG    non-X related IgG

Preparation of IgG
and labeling with
fluorescent dye 1 anti X IgG    non-X related IgG

Virus X in
chronic phase
(patient 2)

anti X IgG    non-X related IgG

Preparation of IgG
and labeling with
fluorescent dye 2 anti X IgG    non-X related IgG

Mixing with acute
serum of virus X

Selection of complexes
stained with dyes 1/2
with FCS cross-correlation
and electric trap in vivo/in vitro infection
PCR cloning

FIGURE 5

METHOD AND DEVICE FOR THE SELECTIVE WITHDRAWAL OF COMPONENTS FROM COMPLEX MIXTURES

The present invention pertains to a method for the withdrawal of one or a few components of a system, a device for performing said method, and uses thereof.

The functional characterization of single molecules or molecular complexes, viruses or individual cells is possible by means of the methods described in Rigler et al. (PCT/EP 94/00117). By means of the method described, information can be obtained about whether, in a complex mixture of a solution or suspension or in a two-dimensional layer, there are contained within very small volume elements ($<10^{-12}$ l) individual molecules or molecular complexes which are subject to particular interactions with defined target molecules.

For many analytical and synthetic problems, it is already a great advantage to know that a sought molecule does exist in a mixture being analyzed. Frequently, however, the problem to be solved by the present invention arises, that is to selectively remove the molecule once recognized as being the desired one in terms of a preparative enrichment, e.g., in order to avoid or to facilitate cloning steps. Another problem in particularly diluted solutions having a concentration of $10^{-12}$ M is to quickly find a volume element as a part of the sample volume in which a representant of the sought substance is present. It is by no means necessary that the sought substance be known. When unknown pathogens or active substances are sought, it may be that only interactions with known substances are known, or interactions with optionally present detector molecules can be postulated.

Methods and devices have been described for the withdrawal of whole cells. The corresponding devices are known as cell sorters. For example, certain cell types of a blood picture can be identified from particular parameters of light scattering or fluorescence, and the cells of a defined specification counted. The cells can be stained with fluorescence-labeled antibodies and differentiated by their surface antigens or classsified by hybridization methods (in situ) due to their nucleic acid contents. After their isolation in droplets, the cells are analyzed in flow and may be selectively separated or fractioned by selective electrostatic deflection of single droplets. Appropriate devices are commercially available and are of great importance in clinical diagnostics and research. PCT/EP 93/03077 discloses a method for separating individual, linearly separated volume elements from a capillary flow.

The object of the present invention is to provide a method which permits to withdraw a small volume element of a solution or suspension from a larger volume element of a sample volume of said solution or suspension at defined space coordinates wherein said small volume element contains a target substance. Such a small volume element can be defined using analytical methods as described in the Rigler et al. application (PCT/EP 94/00117). This involves analyzing extremely small measuring volumes as a part of a larger, surrounding sample volume by confocal illumination of a volume element, excitation by the light used for said illumination, and/or registration of specific fluorescence signals, and concluding therefrom the presence of particular components. Alternatively, said illumination may also be achieved, for example, by the method of near field spectroscopy using apertures which are smaller than the wavelength of the irradiated electromagnetic radiation. The object, to selectively withdraw a sought, detected substance, a particular molecule, a molecular complex or a cell due to their spectral properties, is also to be achieved.

The method according to the invention may be employed to particular advantage for detecting as yet non-identified, unknown pathogens or immunogens. (Unknown) pathogens or immunogens can be characterized and optionally obtained in a preparative manner. A particularly advantageous procedure according to the invention makes use of the fact that pathogens will first proliferate after having infected a host organism without being prevented therefrom by a ready immune defense. Only after a certain period of time has elapsed, the immune defense will establish a humoral immune response, e.g., by the synthesis of various immune globulins (principally IgM, followed by IgG), and later a cellular immune response. Patients suspected to have undergone an infection or contact with an as yet unknown pathogen or immunogen without detectability of known antigen properties with respect to a particular reaction or detectability with known antiserums/antibodies are the starting material for pathogen isolation. Later, in the phase of chronic disease, it is considered that antibodies against the suspected pathogen, e.g., a virus, will have formed in the meantime with the virus level, however, having largely decreased. Serums from this phase of the disease serve to prepare the immuneglobulins.

The fraction of immuneglobulins normally contains only a minor percentage of antibodies directed against the unknown pathogen. The major part of the antibodies is directed against a variety of antigen structures which are not related with the sought specific pathogen/immunogen. Therefore, it is more difficult to characterize the pathogen through an immune complex using serums from one single patient.

However, the sought immune complex can be isolated by recurring to some expected characteristics:

The immune complex contains the mass-determining major portion of a pathogen the mobility of which is between that of a small RNA virus and that of a bacterium.

The pathogen has several antigenic binding sites which are occupied by more than one dye-labeled antibody.

In a preferred procedure (FIG. 5), the antibodies from two patients in the condition of the hypothetically chronic phase can be prepared separately and labeled with different dyes or with dyes to be differentiated by cross correlations. Said at least two patients are selected such that there is a high probability that both patients have been infected by the same pathogen. Since pathogens usually carry a large number of antigenic determinants on the surface/viral envelope, it is likely that the immune complexes formed after reaction with a mixture of differently labeled antiserums will simultaneously comprise the different labeling dyes.

The experiments are performed as illustrated in FIG. 5. Detection of Individual Bacteria by the Binding Specifities of Surface-Expressing Bacteria For a large number of important applications in modern biotechnological research, it would be extremely advantageous and efficient if the detection of a functional biomolecule in a given sample volume in a method could be replaced by the detection of an individual bacterium or virus having functional surface proteins. The decisive advantage is the interesting coupling of a phenotypical expression product, e.g., a natural or recombinant surface protein, to its genetic construction plan. The method, in particular, is to be seen in the context of a preparative use according to the invention by means of which cells or molecular complexes determined to be the sought ones can be separated from an environment.

Determination and Preparative Recovery of the Immunogenic Epitopes of Microorganisms The genome of microorganisms comprises about $10^7$ nucleotides. Subgenic fragments having an average length of 100 amino acids can be expressed according to the method described by shot-gun expression. Taking into account the variation of reading frames (factor 3) and an assumed non-coding counter-strand, $10^8$ recombinant bacterial clones contain 100 copies of each segment. $10^8$ recombinant bacterial clones are contained in 1 ml of a suspension of 1 OD which can be examined individually within about 24 hours, by the method according to the invention, e.g., in terms of their binding properties with IgE or IgE bearing cells from an allergic patient. According to the invention, the correspondingly characterized bacteria are separated, or at least highly enriched, biologically expanded, or the corresponding genome segment is amplified and characterized by enzymatic amplification methods.

Figure 2:
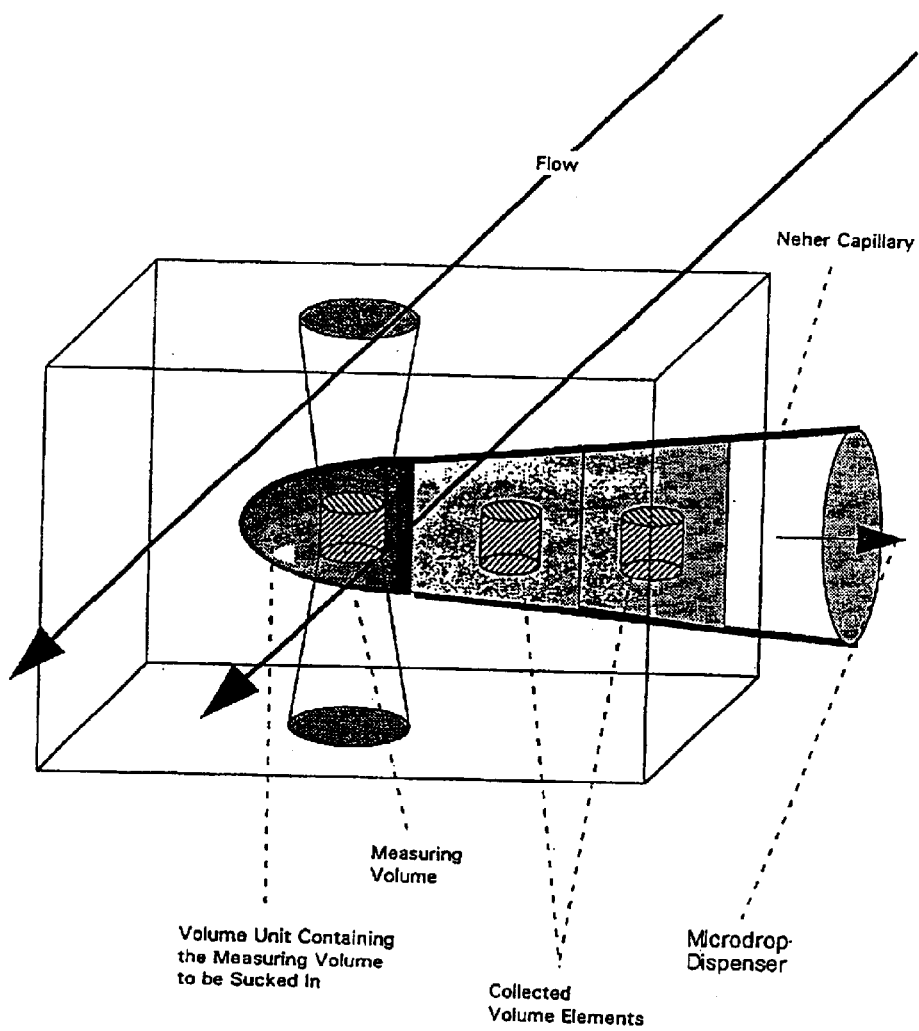
Figure 3:
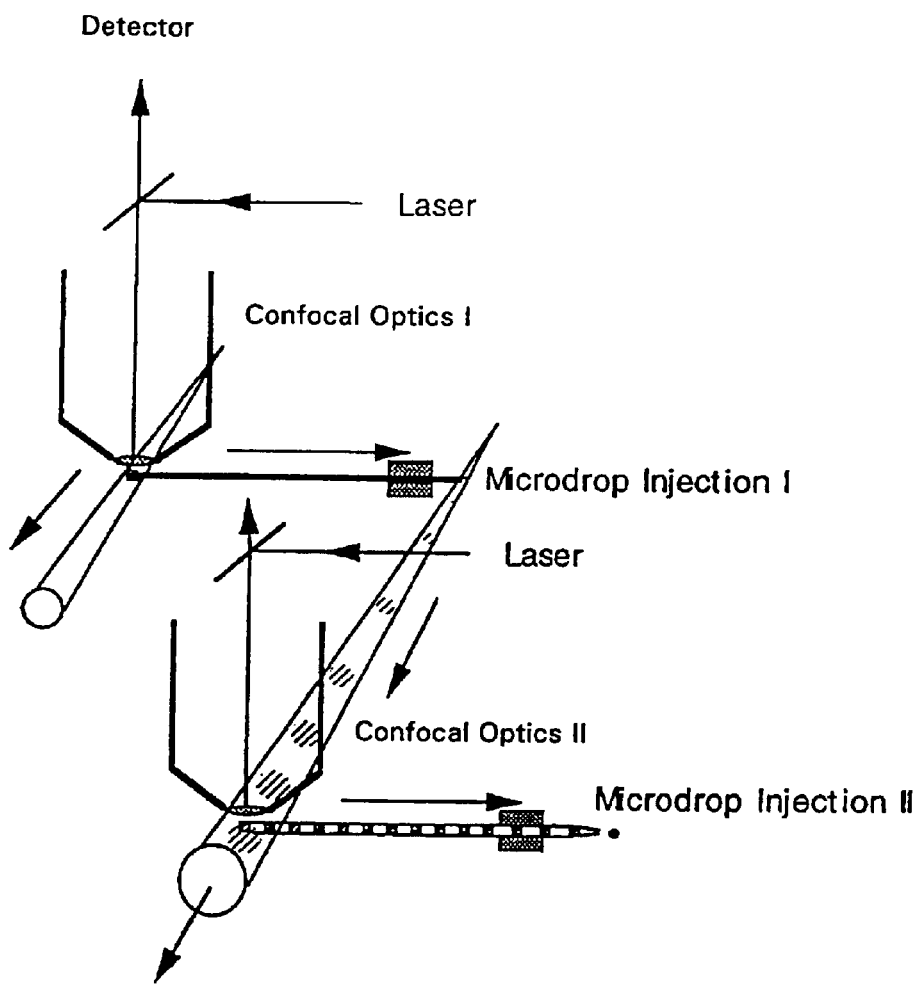
Figure 4:
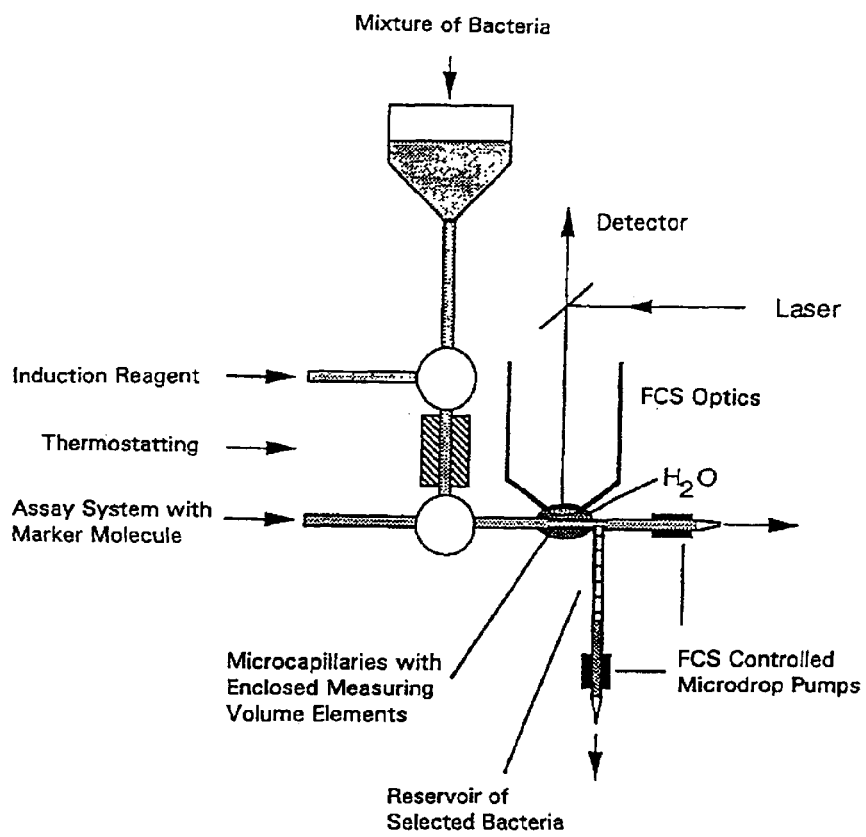

If a corresponding bacterium is detected in the measuring volume element, it can be immediately withdrawn from the mixture, according to the invention, by sucking the volume element surrounding the bacterium/molecular complex through a capillary or separating the molecular complex by electrophoresis, electroosmosis or dipole induction (FIGS. 1 and 2).

An idea on which the invention is based is to employ an electrically, optically or mechanically controlled sucking device the aperture of which is large as compared to the measuring volume, but small as compared to the dimensions of the sample volume, in order to achieve the object of the invention. According to the invention, the electrical, optical or mechanical pumping system is controlled by an FCS-controlled pulse-generator so that a small fraction of the sample volume is separated from the total volume in such a way that a back diffusion can be essentially excluded. This is achieved by electrophoresis, induced dipole moments, electroosmosis, mechanically induced pressure jump, or the pressure of light.

The method permits the withdrawal of one or a few components of a system, such as molecules, molecular complexes, vesicles, micelles, cells, optionally embedded in an associated volume element (withdrawal volume), V ($10^{-9} \geq V \geq 10^{-18}$ l). This volume element is part of a larger volume of an environment which contains the small components to be withdrawn (sample volume). The withdrawal is effected by transferring the component or components to another environment wherein space and time of the withdrawal are determined by an analytical signal which is correlated with the small component to be withdrawn. The analytical methods which may be used are those by which the molecular contents of smallest volume elements ($10^{-14}$ l) can be analyzed as described in the International Application of Rigler et al., PCT/EP 94/00117. The sample volume is connected with a receptor means through a pore of a capillary or a pore of a membrane wall whose smallest aperture D is given by D according to the formula $100 \, \mu m \geq D \geq 0.1 \, \mu m$.

In a preferred embodiment, a capillary is employed as described in Neher et al., Methods in Enzymology, vol. 207, 3–14. This capillary is connected, e.g., with a conveying means, such as a pump, which is capable of drawing off the solution volume surrounding the molecular complex. It is preferred according to the invention to use a mechanically, light pressure or electrically controlled sucking system or a (piezo/isolenoid) pump controlled dispenser system.

Several withdrawals to the same receptor means can be performed in one or more steps wherein the individual withdrawal processes may be performed independently in terms of a gathering process.

In many cases, the electrically controlled withdrawal through a directed transport of the volume element by means of at least one electrical voltage or field strength impulse is preferred. Other embodiments operate mechanically by means of at least one pressure difference impulse and/or by means of at least one light pressure impulse in the direction of the pore aperture using methods as published, e.g., by Weber and Greulich, Int. Rev. Cytol., 1992, 133, pages 1–41. The receptor means may be a capillary the lumen of which is preferably larger than the diameter of the pore or capillary tip the aperture of which is in direct contact with the sample volume. In constantly thin capillaries, electroosmosis can be performed as is common in capillay elektrophoresis since otherwise, in mechanical volume transport, the flow resistance could become disadvantageously large.

In the case of an electrically mediated withdrawal, the sought component in the measuring volume is selectively transferred to the receptor means preferably by means of an electrical field strength impulse by shortly applying an electrical field at least once for electrophoresis of electrically charged components and/or for electroosmosis with coupled transport of electrically neutral molecules. One electrode may be placed in electrically conducting contact with the solution on the side of the sample volume while the other electrode is placed in electrically conducting contact with the solution on the side of the receptor means and the conducting contact between the two compartments is established through the pore. When the withdrawal is effected by means of a well-aimed pressure pulse, the desired transport is caused by at least one short increase of the pressure in the volume outside the receptor compartment as compared to the pressure inside the receptor compartment, and/or by a short reduction of the pressure inside the receptor compartment. Per se known dispensers (Microdrop) or pumping/sucking devices (solenoid pumps, stepping motor controlled pumps) have been found to be useful. Volume elements as small as $\leq 1$ nl can thereby be transferred from a larger volume of a solution or suspension to a receptor compartment by transferring the small volume element through a pore having a diameter of $\leq 100 \, \mu m$ wherein the time and the space coordinate of the withdrawal process is controlled by a correlated analytical system, such as fluorescence correlation spectroscopy (FCS).

Especially a reduced pressure pulse from a piezo-controlled dispenser module the filling volume of which is inside the receptor compartment, and/or a pressure pulse and/or reduced pressure pulse causes that the volume of the receptor means is enlarged, or the sample volume is diminished in favor of the receptor means. According to the invention, transport to the receptor volume ensues. The size of the received volume is controlled by the number of the dispensed droplets or the steps of the stepping motor or the length and intensity of the light pressure pulse.

The hardware/software-coupled on-line operating analyzing system triggers the withdrawal time through the received correlating signal. The withdrawal is performed in the moment when the particle or particles to be withdrawn is/are present within the withdrawal volume with high probability. This needs not necessarily occur in a virtually simultaneous manner with the reception of the positive analytical result. When a molecule, molecular complex, virus or cell has been identified by FCS as a component to be withdrawn, it may be withdrawn immediately or later. This is based on the assumption that the respective component either is present, due to forced transport as described or electrophoretical migration, in a particular place at a defined time shortly after the measurement and can be separated from there electrophoretically or mechanically according to FIGS. 1 and 2; or, when there is no forced translation, is still present near the detection volume from which the component can be separated electrophoretically, optically by light pressure, or mechanically.

Commercial cell sorters are equipped with a system for the isolation of cells following prior analysis which may be coupled, according to the invention, with the analytical method of fluorescence correlation spectroscopy. Usually, cells are guided in a liquid-coated capillary flow through a cuvette which is coupled to a conventional fluorescence measuring device and/or a light-scattering measuring device. In a defined space and time interval behind the measuring device, a standardized continuous division of the thin liquid jet into individual exiting droplets is provided at the end of the capillary by applying a continuous sound frequency. When a cell of a desired cell type passes the cuvette, this cell will be present in one of these droplets after a defined period of time which droplet can be selectively deflected from its trajectory after the isolation by means of a coupled signal, e.g., by means of a pulse in an electrostatic field, and thus can be separated in a separate receptor means. The drawback of this method resides in the fact that in a flowing stream, only an integral fluorescence signal in terms of a pure intensity measurement can be obtained. In contrast, the coupling with the method of fluorescence correlation spectroscopy in small volume elements according to the invention enables a differentiation of the fluorescence signals obtained by their assignment to different molecular sizes and mobilities. This is required, e.g., for distinguishing receptor-bound ligands from free ligands present. According to the invention, the method of fluorescence correlation spectroscopical detection of fluorescing particles, such as molecules, vesicles, cells or molecular complexes, in a mechanically induced capillary flow is employed with a selective sorter device for withdrawal through a pore.

The actual separating process may take place after the passage of individual volume elements through the pore by transferring the measuring volumes yielding a positive registration with an associated volume element to separate receptor means following a defined space and time correlation.

In another preferred embodiment, the FCS measuring process may also take place prior to the exit from the pore of a capillary tip which is coupled with a microdispenser means wherein small measuring volumes with an associated volume element of the environment are collected as droplets in different receptor means by various mechanical or field-induced deflections.

In particular, the time and/or space specific correlation between the analysis of a subvolume of the sample volume (measuring volume) within volume element V and the withdrawal of a desired component by removing the volume element V is effected with the aid of hardware/software. It is effected in such a way that at least one component which has been positively identified in volume element V will be present in the withdrawn volume element V during the withdrawal process. The pore of the receptor means is mechanically approached to the volume element, and/or the volume element V or parts thereof are transported to the pore of the receptor compartment with a predetermined time correlation by transport in the flow or by electrostatic or magnetic field gradients. The analysis may also be performed immediately in front of the pore of the receptor compartment. Preferably, the subvolume (measuring volume) is smaller than the volume element V. This increases the probability that the positively identified component is withdrawn before it has moved too far out of the measuring volume.

The analytical method must meet certain requirements in order that it may be employed in the present method. For example, the signal correlating with the withdrawal process is detected by an optical analytical system which is capable of analyzing specific molecular properties in volume elements as small as $<10^{-14}$ l. This is preferably done by analysis systems based on confocal laser correlation spectroscopy or fluorescence correlation analytics based on near field spectroscopy the signal of which time-controls a selective withdrawal process on-line and in a software-controlled fashion. A number of coupled analytical and withdrawal processes can be sequentially employed in a cascade-like manner according to the invention wherein the withdrawn sample volumes are subsequently again subjected to an analysis with or without an intermediate dilution step, and are again withdrawn after completion of the analysis in enriched form by a second and/or further withdrawal unit.

Such components can be withdrawn which form a complex with at least one reaction partner capable of being spectroscopically detected (indirectly), or which have themselves sufficient fluorescence properties (directly).

Of particular interest is the method in combination with the procedure for withdrawing as yet unidentified (unknown) pathogens according to the invention. The object is to proliferate an isolated pathogen in vivo or to proliferate the genetic material of the pathogen or parts thereof in vitro by amplification of the nucleic acid contained therein in terms of a shot-gun method, and its characterization by sequencing.

Also important is the selected withdrawal of components which have been unknown to date with respect to their molecular nature, such as molecules, cells, vesicles, molecular complexes, which can be functionally identified, e.g., through an enzymatic activity or complex formation.

As outlined in FIG. 5, unknown particles, such as pathogens or immunogens, are withdrawn according to the invention by collecting serums from at least one organism which is infected with the unidentified pathogen. At least one serum (serum 1) is obtained from the phase of an acute infection by the as yet unknown pathogen or immunogen, and at least one other serum (serum 2) is obtained from the same or at least one other organism with the same or a homologous infection in the phase of chronical disease. The unknown pathogen or immunogen from serum 1 is complexed with indirectly or immediately fluorescence-dye labeled antibodies from serum 2, and the complex formed is measured. Important in this connection is cross-correlation, such as described in PCT/EP 94/00117, by which, e.g., the simultaneous binding of different fluorescing ligands, such as antibodies from different organisms, can be measured. The labeling of antibodies may be done immediately by at least one reaction with dyes capable of coupling, or indirectly by reaction with dye-labeled antibody binding domains, in particular protein A derivatives or protein G derivatives. The unidentified pathogenic components may prove to be per se known microorganisms. The detected characteristics are specific interactions with surface-expressed or cytosolic-expressed structural elements of natural or recombinant proteins or peptides or enzymatic activities with fluorescence-labeled target molecules.

The method according to the invention may cause the detection of molecules in very low concentrations. For example, scanning of fetal cells in the maternal blood may be performed. With the method according to the invention, very low concentrations (<$10^{-12}$ M) of fluorescing molecules can be determined. However, the method may become impracticable if, for establishing one or more measuring volumes, too long waiting with unchanged space coordinates is necessary until a sought molecule passes the space element of the measuring volume. This problem also arises with higher concentrations (>$10^{-12}$ M) if the diffusion times are very short as is the case, e.g., with cells and cell-bound molecules. In such cases, the method according to the invention may be modified so that the actual measuring process is preceded by a scanning process in which the space coordinates are varied in a measuring technique continuous or discontinuous in time until a signal of the desired quality is detected. This may be, for instance, the common occurrence of a correlated fluorescence with two different emissions when the cross-correlation method is used. When a signal is detected, the FCS measuring process is started. The duration of a scanning process may be less than one millisecond per measuring process. This is sufficient to establish that the scanned measuring volume or the measuring volumes measured in parallel do not contain the sought component. In this approach, it has to be considered that the absolute values of the average characteristic diffusion times are influenced in a calculatable manner. For example, it may be that fixed molecules (e.g. on fixed bacterial cells) directly and exclusively reflect the variation in time of the relative change of the space coordinates of the measuring volume with respect to the coordinates of the sample volume, or about half of the average dwelling time with mobile small molecules and abrupt changes of the space coordinates since the molecules are already within the measuring volume at the beginning of the measuring process.

Scanning processes preceding the actual measurement become important, e.g., when cell populations are to be analyzed wherein only a fraction of the cells, molecules or molecular complexes bear the properties which determine the withdrawal. This is the case, e.g., in the analysis of evolutively prepared mutant populations of recombinant cells, but also in the analysis of maternal blood for the presence of fetal nucleated erythrocytes which are to be analyzed for particular genes or chromosomal anomalies.

The method is suitable for a method which will be referred to as functional gene extraction in the following. This means the preparation of genetic probes for the identification/detection/cloning of specific functions which are encoded in a whole genome or in a cDNA library. Its application may be exemplified by the functional genome analysis by using phage or bacterial display systems, as well as corresponding applications in evolutive bio-technology. Both examples involve the detection and selection of cells or phages having specific binding properties to particular ligands before a background of non-reacting phages or bacteria.

Thus, the number of screened volume elements significantly increases. In combination with cross-correlation, many volume elements can thus be screened in the $\mu$s to nanosecond range in single and multiarray operation. The dislocation is only interrupted, e.g., when differently colored, correlating signals can be detected in the measured volume element. When this is the case, material parameters of the components, e.g., translational diffusion, can be determined. This time is statistically shorter by a time element to be calculated (about 50%) as compared to the case that a particle must penetrate into the volume element by itself or by forced diffusion. Once a particle is detected, it can be detected a second time by scanning the immediate environment.

According to the invention, the measuring volume may be composed of measuring subvolumes illuminated in parallel by simultaneously illuminating a multitude of measuring volumes by at least one electromagnetic radiation source using at least one holographic grid for generating a multitude of volume elements.

The illumination of a multitude of volume elements in parallel with confocal optics is described in DE 40 35 799. A parallel illumination of measuring volumes the relative distances of which are in the submicron range is not or only unsatisfactorily accomplished by the devices described. The illuminations to be provided in the method according to the invention having dimensions in the lower $\mu$m range and below are accomplished by using holographic grids.

Extended arrays or small volume elements can be illuminated by using holographic grids. According to the invention, the measuring volumes are measured confocally for fluorescence properties of molecules contained therein by using a multitude of pinhole apertures in the image plane, by positioning multiarray detector elements in the image plane, or by using optical fiber bundles to which the light is coupled in the image plane and transferred to photon detectors.

In the highly parallelized illumination of small volume elements, there is the problem of registration of the emitted fluorescence signals from the individual volume elements. In the patent application PCT/EP 04/00117, it is reported that it is possible to illuminate small space elements in parallel and to focus the respective fluorescence signals individually on multiarray detectors by using confocal pinhole aperture systems in the image plane, or to couple the signals into optical waveguides at the position and in lieu of the pinhole apertures and to guide them onto detector elements, or to position the multiarray detectors themselves in lieu of and at the position of the pinhole apertures. There is also described the possibility to illuminate a larger volume element and to combine it with the above described confocal, parallel focussing of small subvolume elements.

However, in high parallelizations, the requirements on the number of detector arrays and the computation effort associated with the data received in the parallel processing become considerable. According to the invention, these problems are solved by collecting the signals integrated over a number of space elements with a registrating device in another mode of coupling small space elements illuminated in parallel. This approach is especially useful in such application in which a large number of volume elements is to be screened;

the computation effort is to be minimized in favor of the computing capacity employed and the computing time;

the number of the volume elements measured in one measurement and thus the total volume measured is to be maximized;

signals from molecules, molecular complexes or cells are to be analyzed in high dilution;

the precision of the space-resolved detection is of minor importance;

the number of the emitted light quantums during diffusion through a single space element is sufficient for a correlation.

According to the invention, at least two measuring volumes in common or assembled in groups are focussed confocally onto at least one detector element of a photon-registrating measuring element in the image plane in the signal registration.

For the detection of fluorescing molecules in very low concentrations, the sample volume is subjected to a scanning process according to the invention prior to the actual measurement and withdrawal of at least one component wherein by a continuous or discontinuous variation in time of the space coordinates of the measuring volume relatively to the space coordinates of the sample volume, the time for detecting a sought particle is shortened. The time interval δt for the measurement of one or more volume elements having defined space coordinates prior to the detection of a sought molecule by its fluorescence measuring signal is shorter than the average dwelling time of the sought molecule within a measuring volume.

A device for performing the method is characterized in that a pore of a porous receptor means is approached closely to the optical measuring volume and said receptor means is connected with a mechanically, optically or electrically controllable withdrawal device. It comprises the arrangement of a closed or open container for receiving a sample volume, coupled with a measuring device for the illumination and/or measurement of a small volume element (measuring volume) by electromagnetic radiation, and at least one connection to at least one second volume element in a receptor means which is in direct contact with the sample volume through an aperture and a liquid phase wherein said aperture is preferably immediately adjacent to said measuring volume.

The method according to the invention may be used, in particular, for the preparative recovery of unknown pathogens, immunogens or organisms which functionally express parts of a genome, and for the analysis and preparative recovery of nucleated fetal cells from maternal blood.

Such problems are connected with methods for the evolutive optimization of peptides and/or proteins by using mutagenesis methods and selection methods, as suggested, for instance, in the International Patent Application PCT/EP 94/00117. It is possible to screen about $10^9$ bacteria for their binding properties to specific dye-labeled substances within 24 hours, e.g., for the presence of a bacterium which expresses a surface protein/peptide capable of interacting with the target molecule of a predetermined concentration. The corresponding bacterium can be cloned from such a reaction mixture according to conventional methods or directly isolated therefrom with the method according to the invention.

Another important field of applications results from the so-called genome project for the functional mapping of gene segments from genomic libraries, cDNA libraries or libraries of subgenic structural elements (Shape Space). In this way, genomic and/or subgenomic segments can be determined among extended collectives by their functions, e.g. their functional binding behavior to target molecules.

The use of the described method of functional assignment of genetically coded peptide segments may become of great importance particularly in allergological research. The assignment of immunodominant epitopes on allergens (e.g. *Aspergillus*, milk protein, α-amylase) is of extraordinarily great importance and to date has been a problem difficult to solve. Typical problems in practice are:

Determination of the IgE-binding molecules among a mixture of substances which is undefined in most cases. For example, it is important to answer the question as to which components of soybean lecithin are immunogenic: the pure substance alone, the pure substance in its interaction with contaminations of the preparation, or the interaction with structures of the receptor organism. According to the invention, the different immunogenic substances can be differentiated in the mixture by means of labeled IgE from patients.

By the expression of subgenic gene segments,
the immunodominant epitopes can be narrowed down, characterized and preparatively recovered with the method mentioned above. With these results,
and with the methods described in DE 41 12 440 C2, evolutively analogous functional molecules can be generated which lack the corresponding immunodominant regions, e.g., attenuated immunogenic α-amylase or washing agent proteases;

the specific epitopes can be readily prepared according to standard methods of genetic engineering, and employed as pure detecting reagents or used for desensibilization.

By means of the method according to the invention, certain problems can be solved which could not be solved to date or which could only be solved with an unreasonably large effort.

Screening of pharmacologically active substances by the binding of known fluorescence-labeled ligands to per se known receptors which may be present on cells or natural or artificial vesicle structures.

There are natural and chemically synthesized drugs with pharmacological activity whose target molecules are unknown. These target molecules can be extracellular molecules (e.g. protease inhibitors), surface membrane receptors (e.g. insulin), soluble receptors as mediators (steroid hormone binding receptors), or cellular soluble structural proteins or enzymes.

Thus, according to the invention, the extremely important problem can be solved, to find, characterize and optionally to isolate the pharmacologically important target molecule of a known drug:

search for orphan receptors;

elucidation of mechanisms of pharmacological action;

search for analogous active substances;

search and differentiation of different receptor molecules, preferably in differentiatable biological targets (different cell differentiation, tumor/non-tumor, disease-associated, non-disease-associated, etc.).

LEGEND OF THE FIGURES

FIG. 1
(Molecule Collector)

The schematical drawing describes the principle of the device in which the components of a small volume element can be transferred from compartment A to a compartment B through a pore which is the open connection between compartments A and B by means of a pressure or reduced pressure pulse or an electrical pulse. One part of this volume element is the measuring volume of $<10^{-14}$ l represented in dark immediately in front of the pore in which the FCS analysis takes place. A cell or a macromolecular complex may also be accessible by an appropriately directed light pressure by means of a laser pulse which is generated perpendicular to the pore diameter and can be directed to transport a complex recognized as a desired one to the receptor means of compartment B.

FIG. 2
(FCS Selection of Individual Microorganisms with Selected Fractioning)

The figure shows the FCS selection of individual microorganisms according to the invention with selected fractioning from a continuously or discontinuosuly moved sample volume. The FCS measuring volume is located immediately in front of the aperture of a capillary pore and is represented by a hatched column within the focussing conus of the FCS illumination or near field illumination. In consecutive steps, measuring volumes identified as positive can each be transported from the sample container to the receptor means together with the surrounding volume in a computer-controlled process. This can be accomplished, e.g., by connecting a microdrop dispenser device or, in a simple embodiment, e.g., by coupling a stepping motor controlled syringe (nl reception/step), or an electrical pulse. Thus, several volume elements can be accumulated in the receptor means during a measurement.

FIG. 3

(Cascade Enrichment)

By serially connecting separation devices as described in FIG. 2, the separation performance can be increased. This is important, for example, when single particles are to be separated free of background, if possible, from a highly complex mixture ($10^{12}$ particles) of, e.g., recombinant bacteria or phages in high concentrations.

FIG. 4

(FCS Selection of Individual Microorganisms)

The figure describes a device for separating bacteria expressing particular properties which can be measured by FCS from mixtures. A mixture of at first non-induced bacteria is fed to a capillary flow system. In a mixing chamber, IPTG, for example, is supplied as an expression inducing reagent. After a sufficiently long flow time, the expression product is supplied with an assay system comprising marker molecules which can subsequently be measured at a defined position by their interaction with a possible expression product. In addition, the figure is to indicate that a positively identified measuring volume may also be withdrawn at a position distant with respect to space and time provided that the space/time coordinates are in a known and defined relationship to one another.

FIG. 5

(Detection and Preparation of New Pathogens)

The figure demonstrates the procedure according to the invention when unknown pathogens are selected which can be detected via cross-correlation by means of FCS wherein the differently labeled antibodies directed against a particular pathogen may preferably be derived from different patients.

What is claimed is:

1. A method for screening substances to determine their pharmacological activity comprising the steps of:
    contacting said substance with a pharmacological target molecule in a sample compartment;
    irradiating that sample compartment to generate a signal functionally related to the interaction of said substance with said pharmacological target using a confocal optical system; and
    withdrawing a withdrawal volume element comprising said interacting substance and target molecule to a receptor compartment wherein the withdrawal is triggered by said signal.

2. The method claim 1, wherein said confocal optical system comprises a multitude of confocal pinhole apertures in the image plane.

3. The method of claim 1, wherein said confocal optical system comprises optical waveguides in the image plane.

4. The method of claim 1, wherein said confocal optical system comprises multiarray detectors in the image plane.

5. The method of claim 1, wherein said signal is produced by a correlated analytical system.

6. The method of claim 5, wherein said correlated analytical system is a fluorescence correlation spectroscopy system.

7. The method of claim 1, wherein said contacting is in the presence of a fluorescently labeled ligand.

8. The method of claim 1, wherein withdrawing said withdrawal volume element is by receptor means selected from the group consisting of a capillary tube or a membrane.

9. The method of claim 8, wherein said capillary tube has a tip connecting said sample compartment to said receptor compartment.

10. The method of claim 9, wherein said tip has an aperture with size D according to the formula $100\ \mu m \geq D \geq 0.1\ \mu m$.

11. The method of claim 8, wherein said membrane has a pore connecting said sample compartment to said receptor compartment.

12. The method of claim 11, wherein said pore has an aperture with size D according to the formula $100\ \mu m \geq D \geq 0.1\ \mu m$.

13. The method of claim 1, wherein said signal generating and withdrawing steps are repeated in series, whereby separately withdrawn volume elements are gathered in said receptor compartment.

14. The method of claim 1, wherein said withdrawing step is performed by a procedure selected from the group consisting of inducing an electrical field between a sample fluid in said sample compartment and a receptor fluid in said receptor compartment, inducing in said sample compartment a pressure greater than in said receptor compartment, inducing a light pressure impulse; and combinations thereof.

15. The method of claim 14, wherein said withdrawing step is performed by briefly applying an electrical field between first and second electrodes, wherein said first electrode contacts said sample fluid in said sample compartment and said second electrode contacts said receptor fluid in said receptor compartment.

16. The method of claim 14, wherein said withdrawing step is performed by inducing a pressure differential by increasing pressure inside said sample compartment and/or by reducing pressure inside said receptor compartment.

17. The method of claim 16, wherein said pressure differential is caused by reducing pressure using a piezo-controlled dispenser module having a filling volume inside said receptor compartment.

18. The method of claim 16, wherein said pressure differential is caused by increasing pressure or reducing pressure caused by change of piston position of a coupled piston pump device.

19. The method of claim 18, wherein said piston pump device is controlled by a stepping motor and the pressure increase amount is controlled by the number of droplets dispensed by steps of the stepping motor.

20. The method of claim 1, wherein said optical system detects said signal, analyzes specific molecular properties of ingredients of said sample, and time-controls the withdrawing on-line under control of computer software.

21. A device for performing the method according to claim 1 comprising
    a sample compartment and a receptor compartment connected by
    receptor means;
    a confocal optical system including signal generating means cooperating with
    withdrawing means, connected to said receptor means, said withdrawing means is controlled mechanically, optically or electrically.

* * * * *